United States Patent [19]
Ansari et al.

[11] Patent Number: 5,891,400
[45] Date of Patent: Apr. 6, 1999

[54] VOLATILE SUBSTANCE DISPENSER

[75] Inventors: H. Rahman Ansari, Old Tappan, N.J.; Barbara Potts; Janet Finnerty, both of Milford, Pa.

[73] Assignee: Quest International B.V., Naarden, Netherlands

[21] Appl. No.: 9,767

[22] Filed: Jan. 20, 1998

[51] Int. Cl.⁶ .................................................. A62B 7/08
[52] U.S. Cl. ...................... 422/125; 422/122; 424/76.4
[58] Field of Search ............................ 422/5, 124, 125, 422/122; 424/76.4

[56] References Cited

U.S. PATENT DOCUMENTS

| | | | |
|---|---|---|---|
| 2,775,006 | 12/1956 | Kranc | 422/125 |
| 3,898,039 | 8/1975 | Lin | 422/125 |
| 4,074,111 | 2/1978 | Hunter | 422/125 X |
| 4,579,717 | 4/1986 | Gyulay | 422/125 |
| 4,647,428 | 3/1987 | Gyulay | 422/125 |
| 4,755,377 | 7/1988 | Steer | 424/76.4 |
| 4,781,895 | 11/1988 | Spector | 422/125 |
| 5,136,684 | 8/1992 | Lonker et al. | 392/392 |
| 5,197,454 | 3/1993 | Lee | 126/9 R |
| 5,220,636 | 6/1993 | Chang | 391/392 |
| 5,578,089 | 11/1996 | Elsamaloty | 44/275 |
| 5,643,866 | 7/1997 | Ansari et al. | 512/4 |

FOREIGN PATENT DOCUMENTS

| | | | |
|---|---|---|---|
| 2 330 031 | 3/1994 | Germany. | |
| 8157864 | of 0000 | Japan | C09J 3/14 |
| 2 192 337 | 1/1988 | United Kingdom | A61L 99/03 |
| 2 286 531 | 8/1995 | United Kingdom | A61L 9/01 |
| WO 97/08282 | 3/1997 | WIPO | C11C 5/00 |

*Primary Examiner*—Krisanne Thornton
*Attorney, Agent, or Firm*—Pillsbury Madison & Sutro LLP

[57] ABSTRACT

A volatile substance dispenser including an inner open-top container for receiving and holding a heat source, such as a candle, and an outer open-top container for receiving and holding a gel containing a vaporizable or diffusable substance that passes from the gel into the surrounding atmosphere after exposure to the thermal energy from the lighted heat source, e.g. candle. The inner container can be glass, ceramic, earthenware or metal, preferably glass with a roughened outer surface.

11 Claims, 2 Drawing Sheets

VOLATILE SUBSTANCE DISPENSER

BACKGROUND OF THE INVENTION

1. Field of the Invention

The invention relates to a dispensing device which provides a controlled release of a perfumed volatilizable substance, such as perfumed oil, insecticide, insect repellents, fumigant, sanitizer or the like, in a binder with assistance from a lighted heat source, such as a lighted candle.

2. Background of Invention

At the present time, candles generally serve as an auxiliary light source during power failures or as some type of novelty device. In either of these cases, only the light from the candle is utilized, not the heat generated by the candle. Thus, there is an unfulfilled market for dispensers which utilize the heat from a candle to serve as further functions other than that of providing light.

The use of devices for dispensing volatile substances is known. The prior art discloses, for example, a combination night light and liquid fragrance vaporizer wherein an electric lamp provides a heat source for vaporizing the active component. Further, it is also known that a plug-in device causing a heating element to assist the dissipation of a volatile substance. However, these devices have limitations such as being complicated and dependent on an electrical outlet for the sources of activation and hence are restricted to a limited area of use. The present invention relates to a volatile substance dispenser wherein a burnable substance such as a candle provides a heat source for vaporizing the volatilizable substance.

Scented candles are popular and their use is increasing. However, their construction imposes considerable limitations and disadvantages on the perfume component. For example, the perfume has to be constructed in such a way that is soluble in the candle material. It is well known that fragrance materials have a limited solubility in wax and hence often the fragrance level in a candle is restricted to a 5–10% range. Furthermore, the wax and perfume must be mixed at elevated temperatures and kept at those temperatures for a considerable length of time during the manufacturing causing thermal degradation and loss of perfume. Even more critical is the unwanted loss of perfume during the burning of the candle whereby a large portion of perfumes is pyrolyzed. The present invention overcomes all these disadvantages by separating the perfume component from the candle yet still exploiting the positive heat energy of the candle to vaporize the perfume.

An object of the invention is to provide a portable volatile substance dispenser that can be utilized at any desired location within a building or elsewhere.

Another object of the invention is to provide an inexpensive and refillable volatile substance dispenser.

A further object of the invention is to provide a volatile substance dispenser utilizing a burnable substance such as a candle as a heat source to vaporize a volatilizable substance.

A still further object of the invention is to provide a burning candle heated volatile substance dispenser wherein the user can control the burn time and the amount of the volatile substance as required.

Other objects, aspects as well as the several advantages will be apparent to those skilled in art upon reading the specification and the appended claims.

SUMMARY OF THE INVENTION

Broadly, the invention comprises a volatile substance dispenser having inner and outer cavities with heat passing from the inner cavity through a wall of thermal conductive material to the outer cavity to vaporize or otherwise diffuse a volatilizable substance in the outer cavity into the surrounding atmosphere.

More specifically, the invention comprises a volatile substance dispenser having a candle placed within an inner cavity and a gel containing a volatile or diffusable substance placed within the outer cavity which is separated from the candle by a wall comprising a thermally conducted material and wherein heat from a burning candle serves to heat the wall and consequently vaporize the volatile substance from the gel.

However, the above gel carrier is not limiting. The volatile substance can also be incorporated in other carriers such as various polymers and absorbent paper, etc. and be dispersed in the environment assisted by a burning candle.

DETAILED DESCRIPTION OF THE INVENTION

Figure 1:
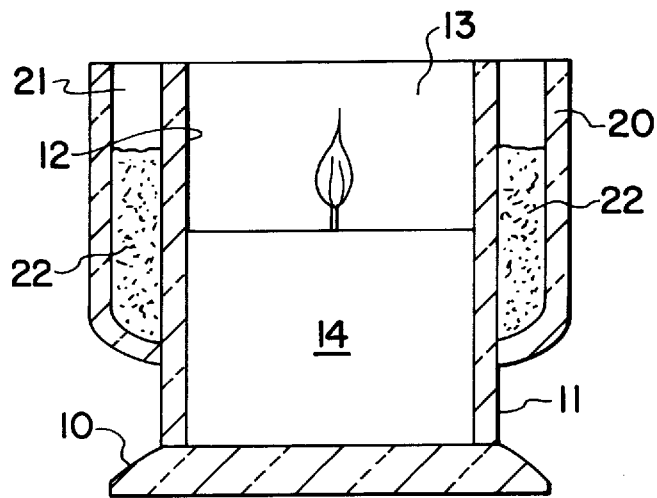
FIG. 1 is a cross-sectional view of an embodiment of a candle-heated volatile substance dispenser in accordance with the present invention.

Referring now to FIG. 1, a candle-heated volatile substance dispenser in accordance with the present invention is shown and generally comprises a base 10 supporting the bottom of container 12 having an open top and forming a cavity 13 for receiving and holding candle 14, an outer container 20 having an open top and forming cavity 21 for receiving and holding gel 22 containing a volatile substance that is vaporized and released to the atmosphere from gel 22 when candle 14 is burning.

As shown in FIG. 1, outer container 20 is joined to container 12 at a lower portion of container 12 but above the bottom of container 12 and above the bottom of candle 14. Containers 12 and 20 preferably are glass and the containers can be formed by molding molten glass as a unitary structure. If desired, the base 10 can be glass and formed as a unitary structure with containers 12 and 20. Also, the base 10 can be a detachable separate unit to provide support for containers 12 and 20. The base 10 is not an essential element of the invention, but is provided for safety and convenience reasons.

Figure 2:
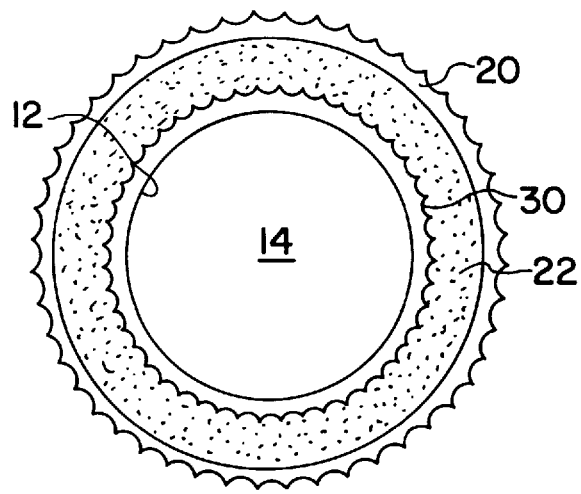
FIG. 2 is an overhead view of the dispenser shown in FIG. 1.

Referring to FIG. 2, the outside wall of container 12 is provided with a plurality of vertical flutes 30 to provide additional heat exchange surface for warming gel 22 to vaporize and dispense the volatile substance in gel 22 to the atmosphere. Other suitable means can be provided on the exterior wall of the container to provide additional heat exchange surface area. Also, as shown, the exterior of gel container 20 can be provided with flutes 31 or other decorative raised portions around the outer surface of container 20.

In use, a user places gel 22 in cavity 21 between outer wall of container 12 and inner wall of container 20. Gel 22 contains a volatilizable substance such as a fragrance, an insect repellent or insecticide, fumigant, sanitizer or the like which is vaporized and released upon heating. The user lights candle 14 and the heat generated by the burning candle heats the wall of container 12 and the heated wall of container 12 provides sufficient heat to vaporize the volatile substance contained in gel 22 and the vapors of the volatile substance produced are released to the atmosphere through the open top of container 20.

Figure 3:
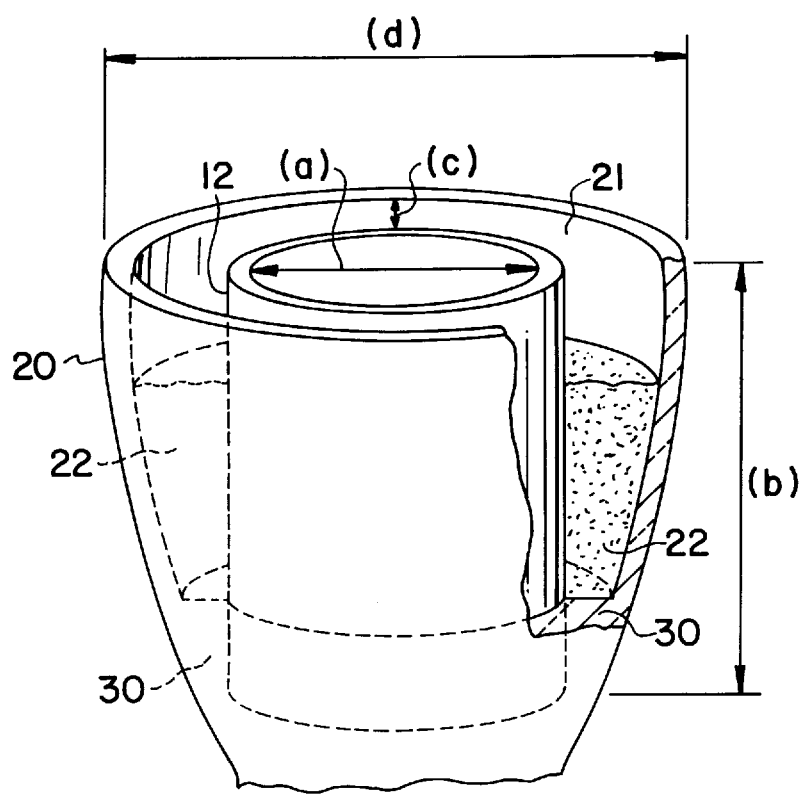
FIG. 3 is a cross-sectional view of another embodiment of a candle-heated volatile substance dispenser according to the invention wherein only a portion of an outer cavity is filled with a gel containing a volatilizable substance.

Now with reference to FIG. 3, another preferred embodiment in accordance with the invention is shown. This embodiment is substantially the same as that of FIG. 1 except that an inert non-volatilizable composition 32 is located in the lower portion of cavity or annulus 21 beneath a layer of gel 22 containing a vaporizable volatile substance. The layer of inert composition 30 is sufficient, usually about ½ inch, so that gel 22 is above the base of the candle in container 12 and in closer proximity to the heat liberated by the lighted candle in container 12.

Gel 22 can be any material which is solid at room temperature and has a vapor pressure less than the vapor pressure of the vaporizable substance contained therein at the vaporization or diffusion temperature. This temperature is the temperature under conditions of actual usage at which the vaporizable substance diffuses into the surrounding atmosphere upon exposure to heat from a lighted candle. Suitable gel compositions 22 that can be used include gels made by using dibenzylidene sorbitol acetal (DBSA) as the gelling agent. Also, gellants such as cabosil (fused silica), gellan gum and various polymers such as polyacrylic acid polymers, can be used. If desired, fragrances can be used as an oil but preferably is used as a gel for safety and overall control.

FIGS. 1–3 also show typical dimensions for the components of the volatile substance dispenser of the invention. Container 12 diameter (a) is about 1½", container 12 height (b) is about 2", container 20 outer diameter (d) is about 2½", container 20 inner diameter (e) is about 2", cavity or annulus 21 dimension (c) is about ½", inert material 32 depth is about ½" and gel 22 fills the remainder of cavity 21 above the inert material. The exact dimensions and configuration of the containers will depend on the vaporizable material in the gel, the thermal energy produced by the heat source and consumer demand.

As used herein the term volatile or vaporizable substance refers to any material released from the gel to the surrounding atmosphere upon exposure to the thermal energy of a lighted candle. Representative examples of suitable materials that can be released from a thermally heated gel according to the invention includes fragrances such as perfumes and incense, vermin-destroying or repelling agents, such as insecticides and insect repellents, medicaments, disinfectants and cleansing agents. Thus, odor-producing agents as well as odor-masking agents can be used. It will be understood that mixtures of agents can be used if desired.

The candle can be comprised of any of the well-known candle making materials. Typical materials are tallow, paraffin wax, carnauba wax, stearic acid and beeswax. The candle can contain the usual additives, colorants and decorations.

The inner and outer containers are preferably a hollow cylindrical shape as shown in FIGS. 1 and 3. The containers, however, also can be triangular, elliptical, conical (e.g. truncated) or rectangular cross-section. It will be apparent to those skilled in the art that the containers can be almost any other geometrical or decorative shape. The exact dimensions and configuration of the containers will depend on the vaporizable material in the gel and the heat source, typically a lighted candle.

The container for holding the candle can be made of any suitable thermally conductive material, particularly the wall separating the candle from the gel containing a volatizable substance in an annulus surrounding the candle-holding container. Typical materials include glass, ceramics, earthenware, metals or other heat conductive materials. The container can be clear, opaque, translucent colored, or otherwise decorated. A preferred candle holder or container is clear or frosted glass having a roughened outer surface. If desired, the outer surface of the candle-holding container can be provided with a plurality of vertical flutes to increase heat transfer from a lighted candle to the gel surrounding the wall of the container. The outer container is preferably made of the same material as the container for holding the candle.

EXAMPLES

The following representative perfumed gel formulations can be used according to the invention.

| GEL SYSTEM I | |
|---|---|
| INGREDIENTS | % BY WEIGHT |
| PERFUME OIL, QUEST INTERNATIONAL | 40.00% |
| IGEPAL CO-630 (1) | 15.00% |
| PROPYLENE GLYCOL | 17.00% |
| DISTILLED WATER | 26.00% |
| DBSA (2) | 2.00% |
| | 100.00% |

PROCEDURE

Premix the perfume oil with the IGEPAL and add the remaining ingredients and heat to 85C.–90C. until a clear solution is obtained. Pour the clear solution at 80C. into molds and the solution will set into a gel upon cooling.

| CTFA Adopted Name | Supplier |
|---|---|
| (1) NONOXYNOL-9 | Rhone-Poulenc |
| (2) MILITHIX 925 | Miliken Chemical |

| GEL SYSTEM II | |
|---|---|
| INGREDIENTS | % BY WEIGHT |
| DISTILLED WATER | 78.75% |
| KELCOGEL (1) | 0.80% |
| POTASSIUM CITRATE (2) | 0.40% |
| KATHON (3) | 0.05% |
| TRITON X-102 SURFACTANT (4) | 10.00% |
| PERFUME OIL, QUEST INTERNATIONAL | 10.00% |
| | 100.00% |

PROCEDURE

Sprinkle the Kelcogel into the water with agitation and heat to 75C. Add the potassium citrate with mixing and cool to 65C. Add the Kathon while mixing. Premix the Triton X-102 and the perfume oil and then add to the batch with mixing. Cool to 55C. and pour into container. Gel will set and clear upon cooling.

| CTFA ADOPTED NAME | SUPPLIER |
|---|---|
| 1) Gellan Gum | KELCO |
| 2) Potassium Citrate | UPI |

| CTFA ADOPTED NAME | SUPPLIER |
| --- | --- |
| 3) Methylchloroisothiazolinone (and) methylisothiazolinone | ROHM & HAAS |
| 4) Octylphenoxy polyethoxy ethanol | UNION CARBIDE |

Although the invention has been explained in relation to its preferred embodiments, it is to be understood that many other possible modifications and variations can be made without departing from the spirit and scope of the invention as hereinafter claimed.

I claim:

1. A volatile substance dispenser comprising:
   (a) an inner container having an open top and inner cavity for receiving and holding a burnable material,
   (b) a flame generated heat source positioned in a lower portion of the cavity within the inner container,
   (c) an outer container having an open top surrounding the inner container and forming an annulus and outer cavity around the inner container for receiving and holding a volatilizable substance, said inner container and said outer container being of unitary construction,
   (d) a gel containing a volatile substance positioned in the annulus and outer cavity so that thermal energy from the heat source in the inner container serves to heat a wall of the inner container and consequently vaporize volatilizable material from the gel in the outer cavity into the surrounding atmosphere.

2. A dispenser according to claim 1 wherein the dispenser is mounted on a base.

3. A dispenser according to claim 1 wherein the inner container is glass and the heat source is a lighted candle.

4. A dispenser according to claim 1 wherein said outer container comprises a base and said inner container comprises an inner container outer wall, said base of said outer container being joined to said inner container outer wall at an intermediate point between the top and the bottom of the inner container so that the gel placed in the outer cavity is above the bottom of the heat source in the inner container.

5. A dispenser according to claim 1 wherein a lower portion of the outer cavity contains a layer of inert material and a layer of gel containing a volatile substance above the inert material.

6. A dispenser according to claim 1 wherein an exterior portion of a wall of the inner container is provided with a plurality of flutes to provide additional heat exchange surface area for passing thermal energy from a burning candle through the wall of the inner container and consequently vaporize volatilizable substance from the gel in the outer cavity.

7. A dispenser according to claim 1 wherein the inner and outer containers are of hollow cylindrical shape.

8. A dispenser according to claim 1 wherein the inner container is glass, ceramic, earthenware, or metal.

9. A dispenser according to claim 1 wherein the volatizable substance is an incense, a perfume, a medicament, an insecticide, an insect repellent, a disinfectant, or fumigant, or mixtures thereof.

10. A dispenser according to claim 8 wherein the outer container is glass, ceramic, earthenware, or metal.

11. A dispenser according to claim 1 wherein the gel is formed with a gelling agent selected from the group consisting of dibenzyllidene sorbital acetal, gellan gum and polyacrylic acid polymers.

* * * * *